(12) United States Patent
Li et al.

(10) Patent No.: US 8,262,576 B2
(45) Date of Patent: Sep. 11, 2012

(54) IMAGING PROBE

(75) Inventors: Pai-Chi Li, Taipei (TW); Bao-Yu Hsieh, Taipei (TW)

(73) Assignee: Pai-Chi Li, Taipei (TW)

( * ) Notice: Subject to any disclaimer, the term of this patent is extended or adjusted under 35 U.S.C. 154(b) by 167 days.

(21) Appl. No.: 12/844,533

(22) Filed: Jul. 27, 2010

(65) Prior Publication Data
US 2011/0301458 A1    Dec. 8, 2011

(30) Foreign Application Priority Data
Jun. 8, 2010   (TW) .............................. 99118612 A

(51) Int. Cl.
*A61B 8/14* (2006.01)
*A61B 8/00* (2006.01)

(52) U.S. Cl. ........................................ 600/459; 600/437
(58) Field of Classification Search .................. None
See application file for complete search history.

(56) References Cited

U.S. PATENT DOCUMENTS

| | | | |
|---|---|---|---|
| 7,587,105 B2 * | 9/2009 | Ashkenazi et al. | 385/13 |
| 2006/0184042 A1 * | 8/2006 | Wang et al. | 600/476 |
| 2007/0073154 A1 * | 3/2007 | Karasawa | 600/459 |

OTHER PUBLICATIONS

Biagi, et al. Efficient Laser-Ultrasound Generation by Using Heavily Absorbing Films as Targets. IEEE Transactions on Ultrasonics, Ferroelectrics, and Frequency Control, vol. 48:Nov. 6, 2001 (1669-1680).*
Davies, et al. Laser-Generated Ultrasound: Its Properties, Mechanisms and Multifarious Applications. Journal of Physics D: Applied Physics, vol. 26:Mar. 1993 (329-348).*
Bao-Yu Hsieh, Sung-Liang Chen, Tao Ling, L. Jay Guo, Pai-Chi Li; Design and fabrication of an integrated intravascular ultrasound/photoacoustic scan head; SPIE Photonics West; Jan. 23, 2010; pp. 104-115; The Moscone Center; San Francisco, CA, USA.

* cited by examiner

*Primary Examiner* — Long V. Le
*Assistant Examiner* — Faizah Ahmed
(74) *Attorney, Agent, or Firm* — WPAT, PC; Justin King

(57) ABSTRACT

An imaging probe is suitable to be inserted into a tubular object so as to detect an interior image of the tubular object. The imaging probe includes a light source excitation assembly, an ultrasonic transducer and a receiver. The light source excitation assembly includes a pulsed laser, a first optical fiber and a cone-shaped reflecting member. The pulsed laser is suitable to generate a pulsed light energy. The cone-shaped reflecting member is suitable to reflect the pulsed light energy to let the pulsed light energy annularly irradiate the inner wall of the tubular object so as to produce a photoacoustic signal. The ultrasonic transducer is suitable to generate an ultrasonic signal. The ultrasonic signal annularly irradiates the inner wall of the tubular object so as to produce an ultrasonic echo signal. The receiver receives the photoacoustic signal and the ultrasonic echo signal.

16 Claims, 3 Drawing Sheets

IMAGING PROBE

CROSS-REFERENCE TO RELATED APPLICATION

This application claims the priority benefit of Taiwan application serial no. 099118612, filed on Jun. 8, 2010. The entirety of the above-mentioned patent application is incorporated herein by reference and made a part of this specification.

BACKGROUND

1. Field of the Invention

The present invention relates to an imaging probe, and more particularly to an imaging probe for detecting photoacoustic image and ultrasound image.

2. Description of the Related Art

Atherosclerotic angiopathies are common diseases, among which the acute ischemic cardiac disease caused by exfoliation of coronary atherosclerotic plaques is the most serious. In order to diagnose and prevent the acute coronary artery disease, it is needed to analyze the structure and the composition of the coronary atherosclerotic plaques.

Currently, intravascular ultrasound imaging technologies are widely used in cardiac microinvasive medical diagnoses. However, an image contrast of soft tissue, fibrous tissue and fat tissue of the plaques provided by a traditional ultrasound image is poor, and thereby exact compositions of the plaques is difficult to be analyzed. Thus, intravascular photoacoustic image is also required. Since absorption coefficients of different compositions of tissues are different, levels of light absorption of different compositions of the tissues are also different, and thereby a contrast of the photoacoustic image is formed. When the tissues irradiated by a pulsed light, the tissues absorb energy and generate thermal expansion effect, then a broadband photoacoustic signal is produced. A receiver receives the photoacoustic signal and converts the photoacoustic signal into an electronic signal. In such way, spatial distributions of the compositions of the tissues are showed by the photoacoustic image.

The photoacoustic image simultaneously has a high contrast of optical image and a deeper penetration depth of ultrasound image. Additionally, the photoacoustic image can provide functional information of the tissues. The ultrasound image can provide structural information of the tissues. Therefore, a stenosis of blood vessel, compositions and positions of the atherosclerotic plaques can be effectively assessed via a combination of the photoacoustic image and the ultrasound image. As a result, the exfoliation risk of the plaques can be assessed, so that an appropriate treatment can be selected to prevent the acute ischemic cardiac disease.

In traditional technology, when an imaging probe is used to obtain the photoacoustic image, the pulsed light energy irradiates along a single direction through a fiber. In order to obtain the intravascular photoacoustic image, a mechanical scanning method is used to obtain a complete image. The mechanical scanning method comprises rotating the imaging probe in the blood vessel so as to obtain a plurality of fragments of the photoacoustic image. Then, the fragments of the photoacoustic image are pieced together to a circled photoacoustic image of the blood vessel. Thus, the imaging probe is required to rotate a lap to obtain a complete photoacoustic image, which is a waste of time and is unable to achieve a function of real-time imaging.

BRIEF SUMMARY

The present invention provides an imaging probe which can simultaneously detect a photoacoustic image and an ultrasound image of an inside of a tubular object and has an advantage of fast imaging.

The present invention also provides an imaging probe having a light source excitation assembly capable of exciting a tubular object to produce a photoacoustic signal. An ultrasound signal is also produced by the light source excitation assembly. As such, the imaging probe can simultaneously detect a photoacoustic image and an ultrasound image of an inside of the tubular object and has an advantage of fast imaging.

To achieve at least one of the above-mentioned advantages, the present invention provides an imaging probe. The imaging probe is suitable to be inserted into a tubular object so as to detect an interior image of the tubular object. The imaging probe includes a light source excitation assembly, an ultrasonic transducer and a receiver. The light source excitation assembly includes a pulsed laser, a first optical fiber and a cone-shaped reflecting member. The pulsed laser is suitable to generate a pulsed light energy. The first optical fiber has a first incident end and a first emitting end. The first incident end receives the pulsed light energy, and the pulsed light energy leaves the first optical fiber via the first emitting end. The cone-shaped reflecting member has a tapered end facing the first emitting end. The cone-shaped reflecting member is suitable to reflect the pulsed light energy emitted from the first emitting end to let the pulsed light energy annularly irradiate an inner wall of the tubular object so as to produce a photoacoustic signal. The ultrasonic transducer surrounds the first optical fiber. The ultrasonic transducer is suitable to generate an ultrasonic signal. The ultrasonic signal annularly irradiates the inner wall of the tubular object so as to produce an ultrasonic echo signal. The receiver has a receiving portion disposed between the first emitting end and the ultrasonic transducer. The receiving portion is configured to receive the photoacoustic signal and the ultrasonic echo signal.

In one embodiment of the present invention, the cone-shaped reflecting member is a micro cone-shaped mirror.

In one embodiment of the present invention, the receiver is a polymer micro-ring resonator for ultrasonic wave detection. The receiver includes a tunable laser, a second fiber and a plurality of micro-rings. The tunable laser is suitable to provide continuous light signals with different wavelengths. The second fiber has a second incident end, a second emitting end and a ring-shaped bending portion. The second incident end receives the continuous light signals, and the continuous light signals leave the second fiber via the second emitting end. The micro-rings are disposed around a periphery of the ring-shaped bending portion. Sizes of micro-rings are different. The receiving portion includes the micro-rings and the ring-shaped bending portion.

In one embodiment of the present invention, the ultrasonic transducer surrounds the first fiber and the second fiber.

In one embodiment of the present invention, the second incident end and the second emitting end of the second fiber are disposed at a same side.

In one embodiment of the present invention, the receiver further includes a light sensor disposed at the second emitting end, so as to receive the continuous light signals emitted from the second emitting end.

In one embodiment of the present invention, material of the micro-rings includes polymer.

In one embodiment of the present invention, the receiving portion of the receiver includes a plurality of ultrasonic receivers. The ultrasonic receivers are arranged in a ring shape and surround the first fiber.

In one embodiment of the present invention, the receiver further comprises a multiplexer coupled with the ultrasonic receivers.

In one embodiment of the present invention, the ultrasonic transducer is a hollow cylinder.

To achieve at least one of the above-mentioned advantages, the present invention further provides an imaging probe. The imaging probe is suitable to be inserted into a tubular object so as to detect an interior image of the tubular object. The imaging probe includes a light source excitation assembly and a receiver. The light source excitation assembly includes a pulsed laser, a first optical fiber and a cone-shaped reflecting member. The pulsed laser is suitable to generate a pulsed light energy. The first optical fiber has a first incident end and a first emitting end. The first incident end receives the pulsed light energy, and the pulsed light energy leaves the first optical fiber via the first emitting end. The cone-shaped reflecting member has a tapered end facing the first emitting end. The cone-shaped reflecting member is suitable to reflect the pulsed light energy emitted from the first emitting end and convert a part of the pulsed laser energy into an ultrasonic signal to let the other part of the pulsed laser energy and the ultrasonic signal annularly irradiate an inner wall of the tubular object. The ultrasonic signal irradiates the inner wall of the tubular object to produce an ultrasonic echo signal. The pulsed laser energy irradiates the inner wall of the tubular object to produce a photoacoustic signal. The receiver has a receiving portion near the first emitting end. The receiving portion is configured to receive the photoacoustic signal and the ultrasonic echo signal.

In one embodiment of the present invention, a surface of the cone-shaped reflecting member has a film. Material of the film includes gold or chromium.

When the imaging probe of the present invention is in use, the pulsed light energy and the ultrasound signal annularly irradiate the inner wall of the tubular object and respectively produce the photoacoustic signal and the ultrasonic echo signal. In such way, the receiver can receive the photoacoustic signal and the ultrasonic echo signal so as to form the complete photoacoustic image and the complete ultrasound image of the inside of the tubular object. Therefore, the imaging probe of the present can achieve the advantage of fast imaging.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

It is to be understood that other embodiment may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings.

Figure 1:
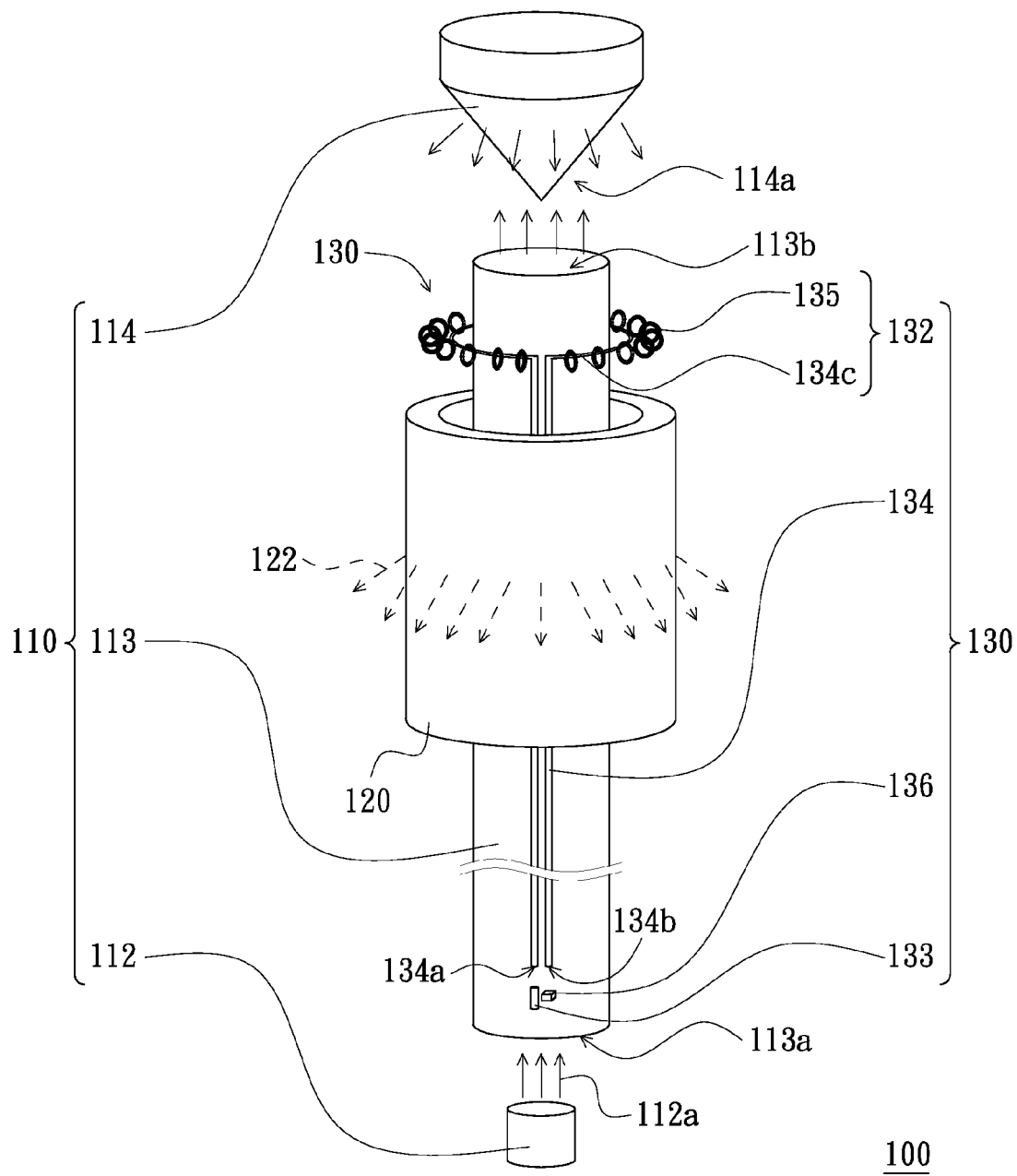
FIG. 1 is a schematic, three-dimensional view of an imaging probe of an embodiment of the present invention.

FIG. 1 is a schematic, three-dimensional view of an imaging probe of an embodiment of the present invention. Referring to FIG. 1, an imaging probe 100 is a miniature probe and is suitable to be inserted into a tubular object (such as blood vessel) so as to detect an interior image of the tubular object. The imaging probe 100 includes a light source excitation assembly 110, an ultrasonic transducer 120 and a receiver 130. The light source excitation assembly 110 is suitable to provide a light signal. The ultrasonic transducer 120 is suitable to generate an ultrasonic signal 122. The receiver 130 receives a photoacoustic signal and an ultrasonic echo signal.

The light source excitation assembly 110 includes a pulsed laser 112, a first optical fiber 113 and a cone-shaped reflecting member 114. The pulsed laser 112 is suitable to generate a pulsed light energy 112a. The first optical fiber 113 is, for example, a multimode fiber, and includes a first incident end 113a and a first emitting end 113b. The first incident end 113a receives the pulsed light energy 112a generated by the pulsed laser 112, and then, the pulsed light energy 112a leaves the first optical fiber 113 via the first emitting end 113b. Additionally, the cone-shaped reflecting member 114 is, for example, a micro cone-shaped mirror, and has a tapered end 114a facing the first emitting end 113b. The cone-shaped reflecting member 114 is suitable to reflect the pulsed light energy 112a emitted from the first emitting end 113b to let the pulsed light energy 112a annularly irradiate the inner wall of the tubular object so as to produce a photoacoustic signal. In other words, the pulsed light energy 112a reflected by the cone-shaped reflecting member 114 can irradiate the whole circled inner wall of the tubular object.

The ultrasonic transducer 120 has, for example, a hollow cylinder shape, and surrounds the first optical fiber 113. The ultrasonic transducer 120 is suitable to generate an ultrasonic signal 122. The ultrasonic signal 122 can annularly irradiate the inner wall of the tubular object so as to produce an ultrasonic echo signal. More specifically, since the ultrasonic transducer 120 has the hollow cylinder shape, the ultrasonic signal 122 generated by the ultrasonic transducer 120 can transmit to the whole circled inner wall of the tubular object.

The receiver 130 has a receiving portion 132 disposed between the first emitting end 113b and the ultrasonic transducer 120. The receiver 130 is configured to receive the photoacoustic signal and the ultrasonic echo signal. In the present embodiment, the receiver 130 is, for example, a polymer micro-ring resonator for ultrasonic wave detection. The receiver 130 includes a tunable laser 133, a second fiber 134 and a plurality of micro-rings 135. The tunable laser 133 is suitable to provide continuous light signals with different wavelengths. The ultrasonic transducer 120 surrounds the first fiber 113 and the second fiber 134. The second fiber 134 has a second incident end 134a, a second emitting end 134b and a ring-shaped bending portion 134c. The second incident end 134a and the second emitting end 134b are disposed on a same side. The ring-shaped bending portion 134c is disposed between the second incident end 134a and the second emitting end 134b and surrounds the first optical fiber 113. The second incident end 134a receives the continuous light signals generated by the tunable laser 133, and the continuous light signals leave the second fiber 134 via the second emitting end 134b. Material of the micro-rings 135 may include polymer. The micro-rings 135 are disposed around a periphery of the ring-shaped bending portion 134c. Sizes of the micro-rings 135 are different so as to respectively couple with lights having different wavelengths. The receiving portion 132, for example, includes the micro-rings 135 and the ring-shaped bending portion 134c. Additionally, the receiver 130 further includes a light sensor 136 disposed at the second emitting end 134b, so as to receive the continuous light signals emitted from the second emitting end 134b.

When the imaging probe 100 is used to detect images, the photoacoustic signal and the ultrasonic echo signal act on the micro-rings 135, and thereby the micro-rings 135 are deformed and light refractive index of the micro-rings 135 are changed. In such way, wavelengths of light capable of being coupled with the micro-rings 135 are changed, so that resonance wavelengths of the continuous light signals are shifted. As a result, the light sensor 136 can detect this change so that the photoacoustic image and the ultrasound image can be obtained according to this change.

In the imaging probe 100 of the present embodiment, the cone-shaped reflecting member 114 is able to let the pulsed light energy 112a annularly irradiate the inner wall of the tubular object so as to produce the photoacoustic signal. Therefore, as long as the pulsed laser 112 generates the pulsed light energy 112a only once, the receiver 130 can completely receive the photoacoustic signal from the whole circled inner wall of the tubular object at the same time, and thereby the image of the whole circled inner wall of the tubular object is obtained. In addition, the ultrasonic signal 122 generated by the ultrasonic transducer 120 is able to annularly irradiate the inner wall of the tubular object, so that the receiver 130 can completely receive the ultrasonic echo signal from the whole circled inner wall of the tubular object at the same time. Therefore, the imaging probe 100 of the present embodiment has an advantage of fast imaging and provides a function of real-time imaging. Moreover, the receiver 130 of the present embodiment uses a single waveguide to transmit a multi-channel signal, and cooperation of the tunable laser and the wavelength multiplexer can switch channels. In other words, different wavelengths can be coupled with the corresponding micro-rings 135, and signals received by different micro-rings 135 can be distinguished via different wavelength signals. Thus, the array type probe of the present embodiment has a simple structure.

It should be noted that, although the imaging probe 100 of the present embodiment is used to detect the intravascular photoacoustic image and the intravascular ultrasound image, the present invention does not limit applications of the imaging probe 100.

Figure 2:
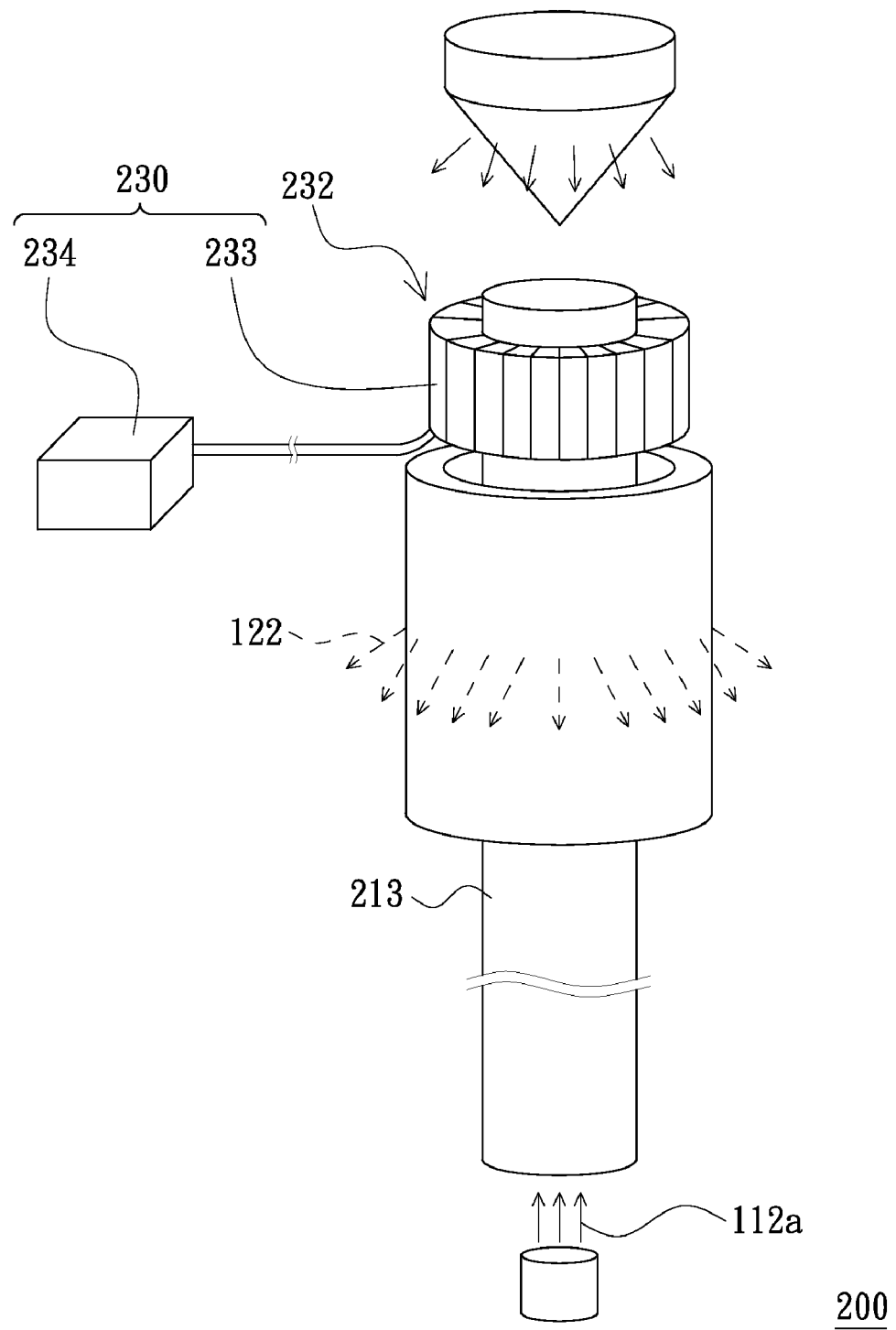
FIG. 2 is a schematic, three-dimensional view of an imaging probe of another embodiment of the present invention.

FIG. 2 is a schematic, three-dimensional view of an imaging probe of another embodiment of the present invention. Referring to FIG. 2, an imaging probe 200 of another embodiment of the present invention is similar to the imaging probe 100, wherein the difference is the receiver. More specifically, a receiving portion 232 of a receiver 230 of the imaging probe 200 includes a plurality of ultrasonic receivers 233. The ultrasonic receivers 233 are arranged in a ring shape and surround a first fiber 213. The receiver 230 further includes a multiplexer 234 coupled with the ultrasonic receivers 233. A photoacoustic signal and an ultrasonic echo signal are received by the ultrasonic receivers 233, and then are transmitted to multiplexer 234. Thereby, a photoacoustic image and an ultrasound image are obtained.

Similar to the imaging probe 100, the imaging probe 200 of the present embodiment also has an advantage of fast imaging.

Figure 3:
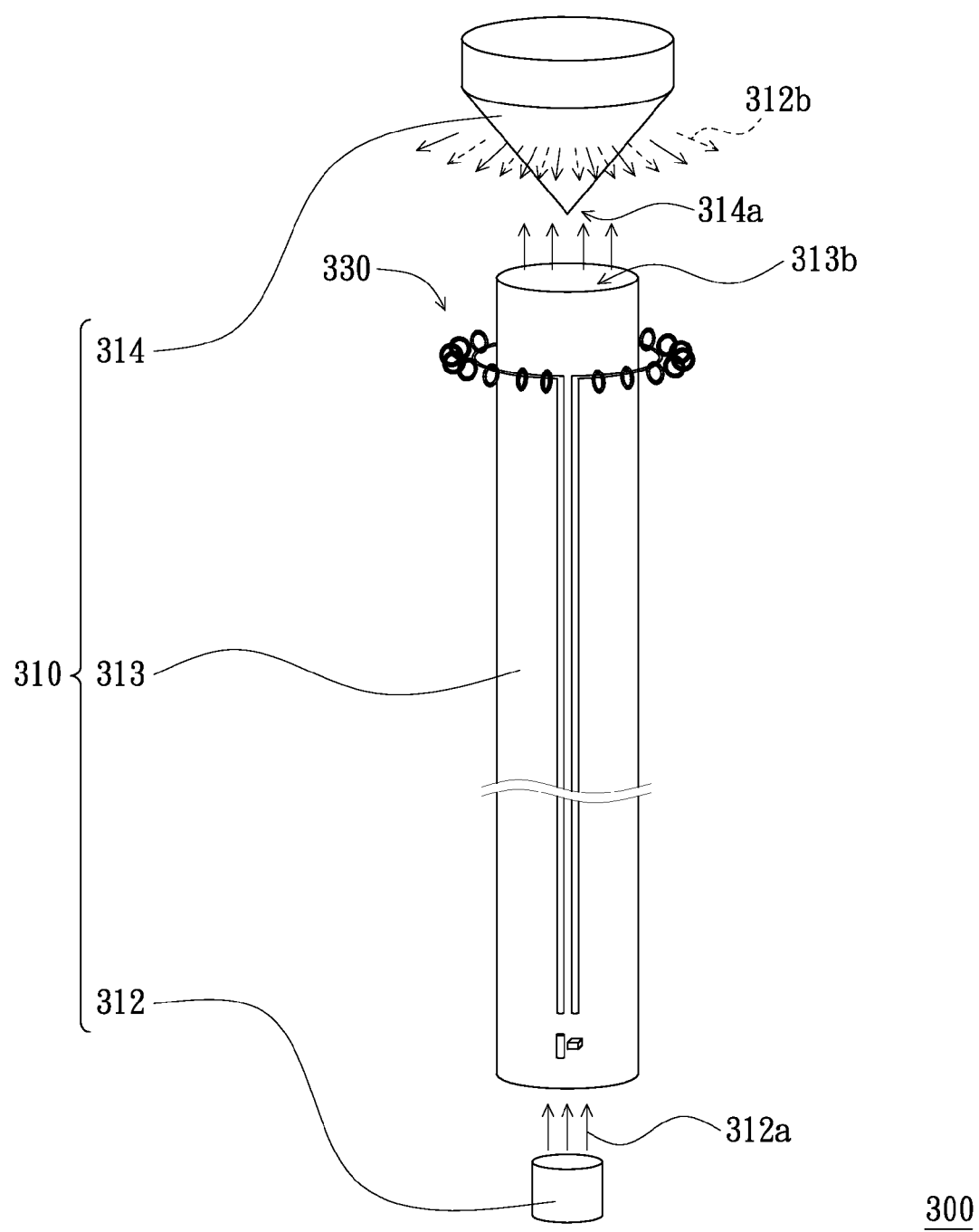
FIG. 3 is a schematic, three-dimensional view of an imaging probe of another embodiment of the present invention.

FIG. 3 is a schematic, three-dimensional view of an imaging probe of another embodiment of the present invention.

Referring to FIG. 3, an imaging probe 300 of another embodiment of the present invention is similar to the imaging probe 100, wherein the difference is that the ultrasonic transducer 120 of the imaging probe 100 is omitted in the imaging probe 300. The imaging probe 300 includes a light source excitation assembly 310 and a receiver 330. The light source excitation assembly 310 is configured for providing a photoacoustic signal and an ultrasonic signal. The receiver 330 is configured for receiving a photoacoustic signal and an ultrasonic echo signal. The receiver 330 of the present embodiment is the same as the receiver 130 described above, details will not be described.

The light source excitation assembly 310 includes a pulsed laser 312, a first fiber 313 and a cone-shaped reflecting member 314. The pulsed laser 312 is the same as the pulsed laser 112 in FIG. 1, the first fiber 313 is the same as the first fiber 113 in FIG. 1, details will not be described. Additionally, the cone-shaped reflecting member 314 is, for example, a micro cone-shaped mirror. The surface of the cone-shaped reflecting member 314 has a film which can convert a part of a pulsed laser energy 312a into an ultrasonic signal 312b. Material of the film can include gold, chromium or other suitable material. In another embodiment, the cone-shaped reflecting member 314 can be made of material which is able to convert a part of the pulsed laser energy 312a into the ultrasonic signal 312b. The cone-shaped reflecting member 314 has a tapered end 314a facing a first emitting end 313b of the first fiber 313. The cone-shaped reflecting member 314 is suitable to reflect the pulsed laser energy 312a emitted from the first emitting end 313b and convert a part of the pulsed laser energy 312a into the ultrasonic signal 312b to let the other part of the pulsed laser energy 312a and the ultrasonic signal 312b annularly irradiate the inner wall of the tubular object. The ultrasonic signal irradiates the inner wall of the tubular object to produce the ultrasonic echo signal. The pulsed laser energy irradiates the inner wall of the tubular object to produce the photoacoustic signal.

In the present embodiment, since the ultrasonic transducer 120 is omitted, the imaging probe 300 not only has all advantages of the imaging probe 100 described above, but also has a simple structure and a low cost. It should be noted that, in another embodiment, the receiver 330 can be replaced by the receiver 230 of the imaging probe 200.

In summary, the imaging probe of the present invention at least includes one of the following advantages.

1. The imaging probe of the present invention can simultaneously detect the photoacoustic image and ultrasound image. The ultrasound image can provide a structural characteristic in blood vessel, and exact compositions of intravascular atherosclerotic plaques can be analyzed via the photoacoustic image. Therefore, the exfoliation risk of plaques can be assessed, and an appropriate treatment can be selected to prevent the acute ischemic cardiac disease.

2. Since the pulsed light energy and the ultrasound signal generated by the imaging probe of the present invention can annularly irradiate the inner wall of the tubular object and respectively produce the photoacoustic signal and the ultrasonic echo signal, the receiver can completely receive the photoacoustic signal and the ultrasonic echo signal at the same time, so as to achieve the advantage of fast imaging.

3. The cone-shaped reflecting member of the imaging probe of one embodiment of the present invention can convert a part of the pulsed laser energy to the ultrasonic signal so that the ultrasonic transducer can be omitted, and thereby the imaging probe has a simple structure and a low cost.

4. In one embodiment, the polymer micro-ring resonator for ultrasonic wave detection is used as the receiver, which makes the imaging probe have a simple structure and a low cost.

The above description is given by way of example, and not limitation. Given the above disclosure, one skilled in the art could devise variations that are within the scope and spirit of the invention disclosed herein, including configurations ways of the recessed portions and materials and/or designs of the attaching structures. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An imaging probe, suitable to be inserted into a tubular object to detect an interior image of the tubular object, comprising:
   a light source excitation assembly comprising:
      a pulsed laser suitable to generate a pulsed light energy;
      a first optical fiber having a first incident end and a first emitting end, the first incident end receiving the pulsed light energy, and the pulsed light energy leaving the first optical fiber via the first emitting end;
      a cone-shaped reflecting member having a tapered end facing the first emitting end, and the cone-shaped reflecting member being suitable to reflect the pulsed light energy emitted from the first emitting end to let the pulsed light energy annularly irradiate an inner wall of the tubular object to produce a photoacoustic signal;
   an ultrasonic transducer surrounding the first optical fiber, the ultrasonic transducer being suitable to generate an ultrasonic signal, and the ultrasonic signal annularly irradiating the inner wall of the tubular object to produce an ultrasonic echo signal; and
   a receiver having a receiving portion disposed between the first emitting end and the ultrasonic transducer, and the receiving portion being configured to receive the photoacoustic signal and the ultrasonic echo signal.

2. The imaging probe as claimed in claim 1, wherein the cone-shaped reflecting member is a micro cone-shaped mirror.

3. The imaging probe as claimed in claim 1, wherein the receiver is a polymer micro-ring resonator for ultrasonic wave detection, and the receiver comprises:
   a tunable laser suitable to provide continuous light signals with different wavelengths;
   a second fiber having a second incident end, a second emitting end and a ring-shaped bending portion, the second incident end receiving the continuous light signals, and the continuous light signals leaving the second fiber via the second emitting end; and
   a plurality of micro-rings disposed around a periphery of the ring-shaped bending portion, sizes of micro-rings being different, and the receiving portion comprising the micro-rings and the ring-shaped bending portion.

4. The imaging probe as claimed in claim 3, wherein the ultrasonic transducer surrounds the first fiber and the second fiber.

5. The imaging probe as claimed in claim 3, wherein the second incident end and the second emitting end of the second fiber are disposed at a same side.

6. The imaging probe as claimed in claim 3, wherein the receiver further comprises a light sensor disposed at the second emitting end to receive the continuous light signals emitted from the second emitting end.

7. The imaging probe as claimed in claim 3, wherein material of the micro-rings comprises polymer.

8. The imaging probe as claimed in claim 1, wherein the receiving portion of the receiver comprises a plurality of ultrasonic receivers, the ultrasonic receivers are arranged in a ring shape and surround the first fiber.

9. The imaging probe as claimed in claim 8, wherein the receiver further comprises a multiplexer coupled with the ultrasonic receivers.

10. The imaging probe as claimed in claim 1, wherein the ultrasonic transducer is a hollow cylinder.

11. An imaging probe, suitable to be inserted into a tubular object to detect an interior image of the tubular object, comprising:
   a light source excitation assembly comprising:
      a pulsed laser suitable to generate a pulsed light energy;
      a first optical fiber having a first incident end and a first emitting end, the first incident end receiving the pulsed light energy, and the pulsed light energy leaving the first optical fiber via the first emitting end; and
      a cone-shaped reflecting member having a tapered end facing the first emitting end, the cone-shaped reflecting member being suitable to reflect the pulsed light energy emitted from the first emitting end and convert a part of the pulsed laser energy into an ultrasonic signal to let the other part of the pulsed laser energy and the ultrasonic signal annularly irradiate an inner wall of the tubular object, the ultrasonic signal irradiating the inner wall of the tubular object to produce an ultrasonic echo signal, and the pulsed laser energy irradiating the inner wall of the tubular object to produce a photoacoustic signal; and
   a receiver having a receiving portion near the first emitting end, and the receiving portion being configured to receive the photoacoustic signal and the ultrasonic echo signal, wherein the receiver is a polymer micro-ring resonator for ultrasonic wave detection, and the receiver comprises:
      a tunable laser suitable to provide continuous light signals with different wavelengths;
      a second fiber having a second incident end, a second emitting end and a ring-shaped bending portion, the second incident end receiving the continuous light signals, and the continuous light signals leaving the second fiber via the second emitting end; and
      a plurality of micro-rings disposed around a periphery of the ring-shaped bending portion, sizes of micro-rings being different, and the receiving portion comprising the micro-rings and the ring-shaped bending portion.

12. The imaging probe as claimed in claim 11, wherein a surface of the cone-shaped reflecting member has a film, and material of the film comprises gold or chromium.

13. The imaging probe as claimed in claim 12, wherein the cone-shaped reflecting member is a micro cone-shaped mirror.

14. The imaging probe as claimed in claim 11, wherein the second incident end and the second emitting end of the second fiber are disposed at a same side.

15. The imaging probe as claimed in claim 11, wherein the receiver further comprises a light sensor disposed at the second emitting end to receive the continuous light signals emitted from the second emitting end.

16. The imaging probe as claimed in claim 11, wherein material of the micro-rings comprises polymer.

* * * * *